US009078661B2

(12) United States Patent
Gallo

(10) Patent No.: US 9,078,661 B2
(45) Date of Patent: Jul. 14, 2015

(54) ABLATOR WITH IMPROVED CUTTING TIP

(75) Inventor: David P. Gallo, Naples, FL (US)

(73) Assignee: ARTHREX, INC., Naples, FL (US)

( * ) Notice: Subject to any disclaimer, the term of this patent is extended or adjusted under 35 U.S.C. 154(b) by 1134 days.

(21) Appl. No.: 13/025,725

(22) Filed: Feb. 11, 2011

(65) Prior Publication Data

US 2011/0196367 A1  Aug. 11, 2011

Related U.S. Application Data

(60) Provisional application No. 61/303,541, filed on Feb. 11, 2010.

(51) Int. Cl.
*A61B 18/14* (2006.01)
*A61B 18/00* (2006.01)

(52) U.S. Cl.
CPC ... *A61B 18/1477* (2013.01); *A61B 2018/00601* (2013.01); *A61B 2218/002* (2013.01)

(58) Field of Classification Search
USPC .................................................. 606/41, 45–50
See application file for complete search history.

(56) References Cited

U.S. PATENT DOCUMENTS

| 5,277,696 | A  | * | 1/1994 | Hagen | 606/49 |
|---|---|---|---|---|---|
| 5,401,274 | A  | * | 3/1995 | Kusunoki | 606/41 |
| 5,531,743 | A  | * | 7/1996 | Nettekoven et al. | 606/41 |
| 5,741,250 | A  | * | 4/1998 | Garito et al. | 606/45 |
| 6,102,907 | A  | * | 8/2000 | Smethers et al. | 606/40 |
| 6,106,524 | A  | * | 8/2000 | Eggers et al. | 606/50 |
| 6,379,350 | B1 | * | 4/2002 | Sharkey et al. | 606/41 |
| 6,921,399 | B2 | * | 7/2005 | Carmel et al. | 606/41 |
| 2007/0149965 | A1 |  | 6/2007 | Gallo et al. |  |

* cited by examiner

*Primary Examiner* — Michael Peffley
(74) *Attorney, Agent, or Firm* — Akerman LLP; Michael K. Dixon

(57) ABSTRACT

An ablator having an electrode positioned at a distal end is disclosed. The ablator may be configured such that the ablator includes an inner shaft having a plurality of distal slots therein and contained within an outer hollow shaft. The inner shaft may extend distally from a distal end of the outer, hollow shaft. The configuration of the distal end of the ablator may increase the operating efficiency of the ablator by reducing the power requirements.

24 Claims, 4 Drawing Sheets

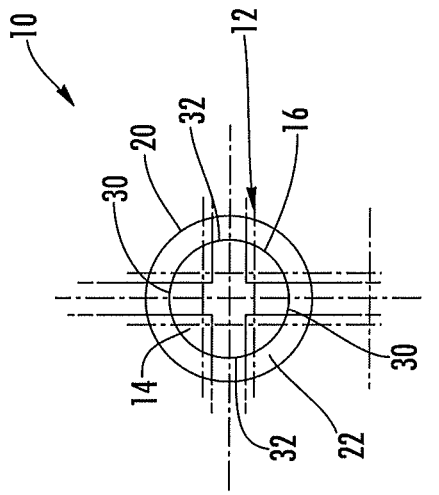
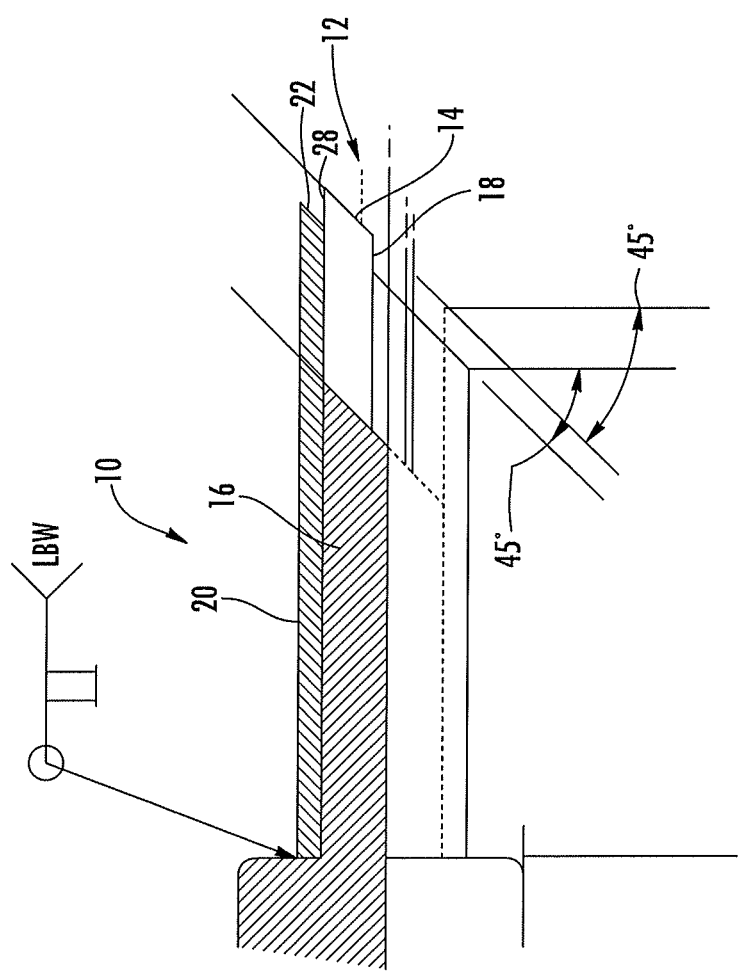

ABLATOR WITH IMPROVED CUTTING TIP

CROSS-REFERENCE TO RELATED APPLICATION

This patent application claims the benefit of U.S. Provisional Patent Application No. 61/303,541, filed Feb. 11, 2010, which is incorporated by reference in its entirety.

FIELD OF THE INVENTION

The invention relates to ablators incorporating electrodes useful in arthroscopy, and more particularly, to ablators with electrodes positioned at a distal end for use in arthroscopy.

BACKGROUND

Arthroscopy ablation has been used to remove biological tissue through a minimally invasive surgical procedure to improve patient recovery. Ablation causes the destruction of targeted cells through the application of heat formed from voltage applied to the targeted cells. The ablation destroys the cells but retains the cell structure.

SUMMARY OF THE INVENTION

This invention is directed to an ablator that includes an enhanced distal tip configured to require less power to operate. The ablator may be configured for use in arthroscopy ablation. Arthroscopy ablation is performed using a conductive fluid media, such as saline, or ringers lactate solutions. The ablator is configured to be used in conjunction with these conductive fluid medias. The ablator may be a monopolar device and may have an electrode positioned at a distal end. The ablator may be configured such that the ablator includes an inner shaft forming an electrode and having a plurality of distal slots therein. The inner shaft may be contained within an outer hollow shaft surrounding the inner shaft. The inner shaft may extend distally from a distal end of the outer, hollow shaft. The configuration of the distal end of the ablator may increase the operating efficiency of the ablator by reducing the power requirements.

In at least one embodiment, the ablator may be formed from a handle, an inner shaft forming an electrode that is supported by the handle and an outer sleeve surrounding at least a portion of the inner shaft and in contact with the inner shaft. The inner shaft may include at least one slot in a distal end of the inner shaft. In one embodiment, the inner and outer sleeves may be welded together. The inner and outer sleeves may be formed as a single component using metal injection molding. The inner shaft may include a plurality of slots extending from a distal end partially into the inner shaft. The plurality of slots may extend from an outer surface of the inner shaft radially through the inner shaft. The plurality of slots may include two slots positioned generally orthogonal to each other. The plurality of slots may extend axially into the inner shaft from the distal end of the inner shaft a distance up to about 0.020 inch. The outer sleeve may be covered by an insulative shrink tube radially outward from the outer sleeve for insulative purposes. The insulative shrink tube may be offset from the distal end of the inner shaft to expose the distal end of the inner shaft. In one embodiment, a distal end of the inner shaft may be positioned at about 45 degrees relative to a longitudinal axis of the inner shaft, and in another embodiment, the distal end of the inner shaft may be positioned at about 90 degrees relative to a longitudinal axis extending through the handle.

These and other embodiments are described in more detail below.

BRIEF DESCRIPTION OF THE FIGURES

FIG. 2 is a partially cross-sectional detail view of an area proximal to a distal end of the ablator taken at detail 2-2 in FIG. 1.

FIG. 3 is an end view of the distal end of the ablator of FIG. 1.

DETAILED DESCRIPTION OF THE FIGURES

Figure 1:
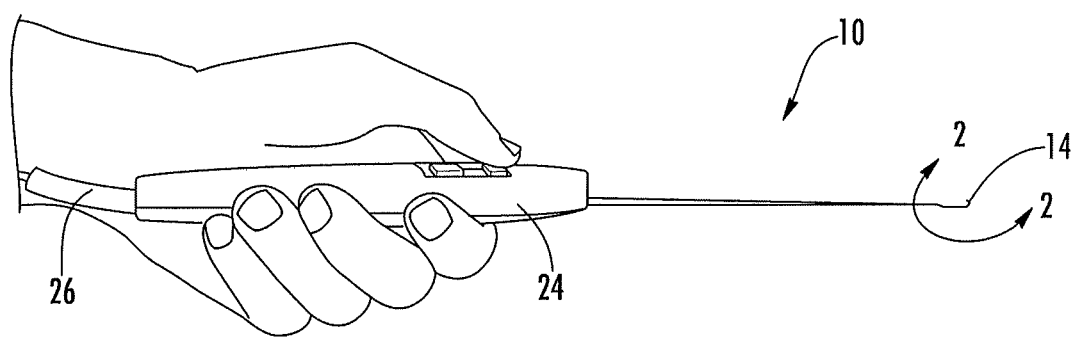
FIG. 1 is a perspective view of an ablator.
Figure 5:
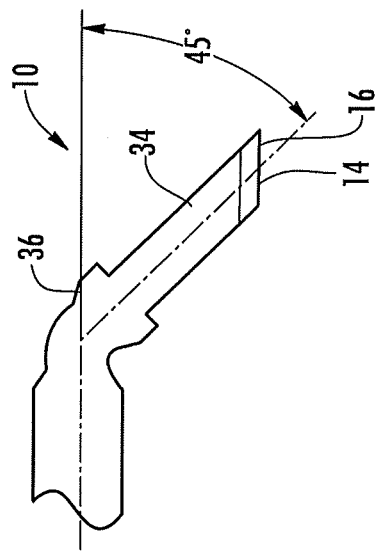
FIG. 5 is a detail view of the distal end taken at detail 5 in FIG. 4.

As shown in FIGS. 1-9, this invention is directed to an ablator 10 that includes an enhanced distal tip configured to require less power to operate. The ablator 10 may be configured for use in arthroscopy ablation. Arthroscopy ablation is performed using a conductive fluid media, such as saline, or ringers lactate solutions. The ablator is configured to be used in conjunction with these conductive fluid medias. The ablator 10 may be a monopolar device and may have an electrode 12 positioned at a distal end 14. The ablator 10 may be configured such that the ablator 10 includes an inner shaft 16 forming an electrode and having a plurality of distal slots 18 therein. The inner shaft 16 may be contained within an outer hollow shaft 20 surrounding the inner shaft 16. The inner shaft 16 may extend distally from a distal end 22 of the outer, hollow shaft 20. The configuration of the distal end 22 of the ablator 10 may increase the operating efficiency of the ablator 10 by reducing the power requirements.

The ablator 10 may be formed from a handle 24, as shown in FIG. 1, configured to support the inner shaft 16 and the outer sleeve 20. The handle 24 may include any appropriate controls thereon. The shaft 16 may be attached directly to the handle 24 or may be configured such that the shaft 16 is attached within the handle 24 to other elements of the ablator 10 that are in turn supported by the handle 24. The handle 24 may contain portions of a power cord 26 in communication with the inner shaft 16. The handle 24 may have any appropriate configuration and may be configured ergonomically to fit within the hand of a user. The handle 24 may be formed from any appropriate material. The material forming the handle 24 may be an insulative material. The ablator 10 may have any appropriate length, which may vary depending on the intended application.

Figure 7:
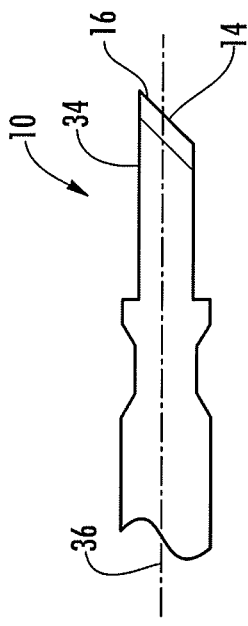
FIG. 7 is a detail view of the distal end taken at detail 7 in FIG. 6.
Figure 4:
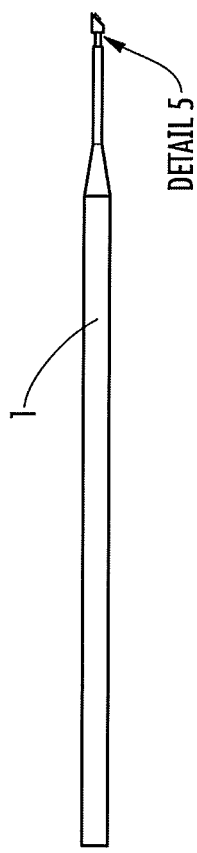
FIG. 4 is a side view of an alternative embodiment of an ablator with a 45 degree distal surface on the distal end of the electrode.
Figure 6:
FIG. 6 is a side view of an alternative embodiment of an ablator with a 90 degree distal surface on the distal end of the electrode.
Figure 9:
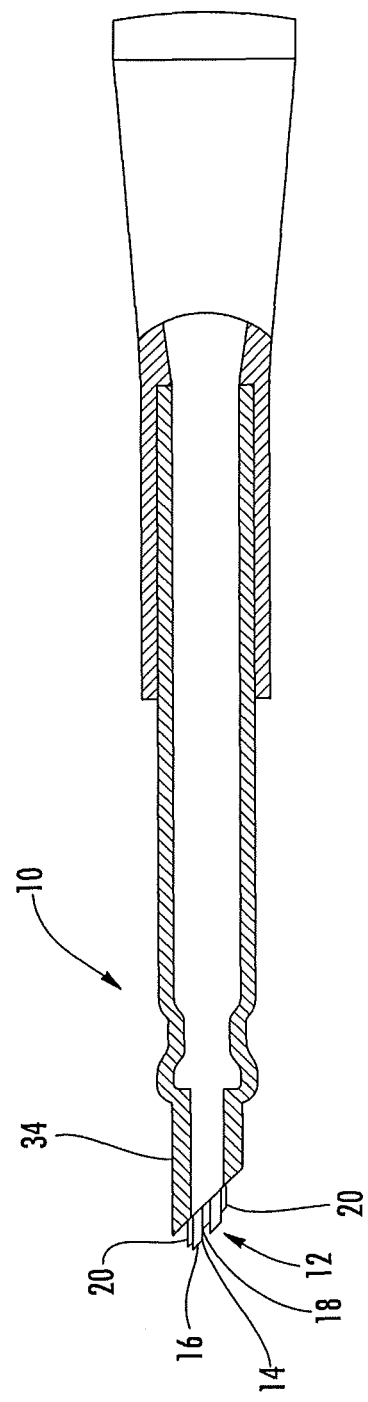
FIG. 9 is a detail view of the distal end taken at detail 9 in FIG. 8.

The inner shaft 16 of the ablator 10 may be supported by the handle 24. The inner shaft 16 may include at least one slot 18 in the distal end 14 of the inner shaft 16, as shown in FIGS. 2, 3 and 9. The slot 18 increases the number of edges at the distal end 14, thereby increasing effectiveness of the ablator 10. In addition, the slot 18 reduces the surface area at the distal end 14, thereby reducing the power requirements for the ablator 10. The inner shaft 16 of the ablator 10 may be formed from a generally elongated shaft. The inner shaft 16 may be formed from many different kinds of materials, such as, but not limited to, aluminum, titanium, or stainless steel. The inner shaft 16 may include a plurality of slots 18 extending from the distal end 14 partially into the inner shaft 16. In at least one embodiment, the slots 18 may extend axially into the inner shaft from the distal end of the inner shaft a distance up to about 0.020 inch. The depth of the slots 18 may vary in other embodiments. The plurality of slots 18 may extend from an outer surface 28 of the inner shaft 16 radially through the inner shaft 16. The plurality of slots 18 may include two slots 30, 32 positioned generally orthogonal to each other, such as shown in FIG. 3. The distal end 14 may be positioned at about 45 degrees, as shown in FIGS. 2, and 6, relative to a longitudinal axis 36 of the inner shaft 16. In an alternative embodiment, as shown in FIG. 7, the distal end 14 may be positioned at about 90 degrees relative to a longitudinal axis 36 extending through the handle 24.

The inner shaft 16 may have a running fit with the outer sleeve 20. The inner and outer sleeves 16, 20 may be mechanically coupled together via one or more welds, silver solder, brazing or other appropriate methods. An outer diameter of the inner shaft 16 may be between about 0.018 inch and 0.028 inch. In at least one embodiment, an outer diameter of the inner shaft may be about 0.023 inch. The outer sleeve 20 may have an inner diameter that is slightly larger than the outer diameter of the inner shaft 16. The outer diameter of the outer sleeve 20 may be between about 0.027 inch and about 0.037 inch. In at least one embodiment, the outer diameter of the outer sleeve 20 may be about 0.032 inch. In one embodiment, the outer sleeve 20 may be only between about 0.25 length and 0.312 inch in length and attached to a shoulder on the inner shaft 16 proximal to the distal end. The shoulder may be positioned a distance from the handle 24 between about two inches and about six inches from a distal end of the handle 24, but other lengths may be used as well.

The outer sleeve 20 may be positioned radially outward from the inner shaft 16. In at least one embodiment, the inner shaft 16 may be concentric with the outer sleeve 20. The outer sleeve 20 may have a distal surface that is aligned with a distal surface of the inner shaft 16. In one embodiment, both the inner shaft 16 and the outer sleeve 20 may be aligned at 45 degrees relative to the longitudinal axis 36. In other embodiments, the distal ends of the inner shaft 16 and the outer sleeve 20 may be orthogonal to the longitudinal axis 36 or other configurations. A distal end of the outer sleeve 20 may be offset proximally from a distal end of the inner shaft 16. In one embodiment, the outer sleeve 20 may be offset proximally from a distal end of the inner shaft 16 about 0.005 inch, and may be offset other distances in other embodiments. The outer sleeve 20 may extend over a portion of the slots 18 in the inner shaft 16, thereby protecting the insulative shrink tube 34 from direct exposure to the heat generated by the distal end 14 of the inner shaft 16. The outer sleeve 20 may be formed from materials, such as, but not limited to, aluminum, titanium, or stainless steel. The inner and outer sleeves 16, 20 may be formed as a single component using various manufacturing processes, such as use of metal injection molding or other appropriate manufacturing method.

Figure 8:
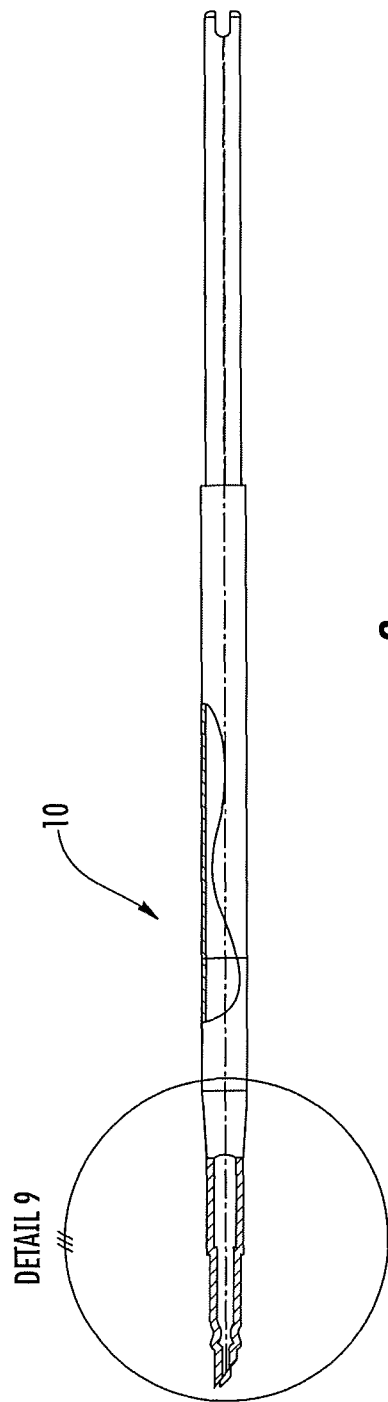
FIG. 8 is a side view of embodiment shown in FIG. 4 together with a heat shrink layer applied to an outer surface of the outer sleeve.

The ablator 10 may also include an insulative shrink tube 34, as shown in FIGS. 8 and 9, positioned radially outward from the outer sleeve 20 to insulate the ablator 10. Use of the shrink tube 34 may enable the ablator 10 to be formed in very small sizes thereby enabling the ablator 10 to be inserted into very small cavities in a patient. The shrink tube 34 may be used to insulate and protect the ablator 10. The shrink tube 34 may be a heat shrink tube sized such that the heat shrink tube may be slid over the outside of the outer sleeve 20 and once subjected to heat, shrunk in size to conform to an outer surface of the outer sleeve 20. The shrink tube 34 may extend from the handle 24 to the distal end 14. The shrink tube 34 may be offset from the distal end 14 of the inner shaft 16 to expose the distal end 14 of the inner shaft 16. The shrink tube 34 may be offset from the distal end 14 of the inner shaft 16 a distance of about 0.020 inch to expose the distal end 14 of the inner shaft 16. In another embodiment, the shrink tube 34 may extend to the distal end of the outer sleeve 20. In yet another alternative embodiment, an insulator, such as, but not limited to, a sprayed insulative coating such as a powder coat material or an injection molding material such as a liquid crystal polymer (LCP) may be used to coat the outer surface of the outer sleeve 20 proximal to the distal end. The shrink tube 34 may be formed from any appropriate material, such as, but not limited to, polyolefin, UV-reactive PVC, PTFE, FEP, PFA, ETFE, KYNAR, NEOPRENE, and VITON. The shrink tube 34 may have shrink ratios such as, but not limited to, 1.2:1 to 4:1.

During use, the ablator 10 may be used to remove select tissue from an ablation site in a patient. Once the ablator 10 is activated, arcing may occur at the edges of the material forming the slots 18 in the inner shaft 16. The inner shaft 16 may be placed in contact with select tissue causing the select tissue to heat, denature and explode, thereby removing the select tissue.

The foregoing is provided for purposes of illustrating, explaining, and describing embodiments of this invention. Modifications and adaptations to these embodiments will be apparent to those skilled in the art and may be made without departing from the scope or spirit of this invention.

I claim:

1. An ablator, comprising:
   a handle;
   a solid inner shaft forming an electrode that is supported by the handle;
   an outer sleeve surrounding at least a portion of the solid inner shaft;
   wherein the solid inner shaft includes at least one slot in a distal end of the solid inner shaft and wherein the at least one slot extends across the distal end of the solid inner shaft; and
   an insulative shrink tube radially outward from the outer sleeve.

2. The ablator of claim 1, wherein the solid inner shaft includes a plurality of slots extending from a distal end partially into the solid inner shaft.

3. The ablator of claim 2, wherein the plurality of slots extend from an outer surface of the solid inner shaft radially through the solid inner shaft.

4. The ablator of claim 3, wherein the plurality of slots comprise two slots positioned generally orthogonal to each other.

5. The ablator of claim 4, wherein the plurality of slots extend axially into the solid inner shaft from the distal end of the solid inner shaft a distance up to about 0.020 inch.

6. The ablator of claim 1, wherein the insulative shrink tube is offset from the distal end of the solid inner shaft to expose the distal end of the solid inner shaft.

7. The ablator of claim 6, wherein the insulative shrink tube is offset from the distal end of the solid inner shaft a distance of about 0.020 inch to expose the distal end of the solid inner shaft.

8. The ablator of claim 1, wherein an outer diameter of the solid inner shaft is between about 0.018 inch and 0.028 inch.

9. The ablator of claim 1, wherein an outer diameter of the solid inner shaft is about 0.023 inch.

10. The ablator of claim 1, wherein an outer diameter of the outer sleeve is between about 0.027 inch and 0.037 inch.

11. The ablator of claim 1, wherein an outer diameter of the outer sleeve is about 0.032 inch.

12. The ablator of claim 1, wherein the inner and outer sleeves are formed from stainless steel.

13. The ablator of claim 1, wherein the inner and outer sleeves are welded together.

14. The ablator of claim 1, wherein the inner and outer sleeves are formed as a single component using metal injection molding.

15. The ablator of claim 1, wherein the distal end of the solid inner shaft is positioned at about 45 degrees relative to a longitudinal axis of the solid inner shaft.

16. The ablator of claim 1, wherein the distal end of the solid inner shaft is positioned at about 90 degrees relative to a longitudinal axis extending through the handle.

17. An ablator, comprising:
    a handle;
    a solid inner shaft forming an electrode that is supported by the handle;
    an outer sleeve surrounding at least a portion of the solid inner shaft and in contact with the solid inner shaft;
    wherein the solid inner shaft includes a plurality of slots extending from a distal end of the solid inner shaft partially into the solid inner shaft and each of the slots extends across the distal end of the cylindrical solid inner shaft; and
    an insulative shrink tube radially outward from the outer sleeve.

18. The ablator of claim 17, wherein the plurality of slots comprise two slots positioned generally orthogonal to each other.

19. The ablator of claim 17, wherein the distal end of the solid inner shaft is positioned at about 45 degrees relative to a longitudinal axis of the solid inner shaft.

20. The ablator of claim 17, wherein the distal end of the solid inner shaft is positioned at about 90 degrees relative to a longitudinal axis extending through the handle.

21. The ablator of claim 17, wherein the plurality of slots extend axially into the solid inner shaft from the distal end of the solid inner shaft a distance up to about 0.020 inch.

22. The ablator of claim 17, wherein the insulative shrink tube is offset from the distal end of the solid inner shaft to expose the distal end of the solid inner shaft.

23. The ablator of claim 17, wherein the inner and outer sleeves are welded together.

24. The ablator of claim 17, wherein the inner and outer sleeves are formed as a single component using metal injection molding.

* * * * *